May 4, 1965 H. KERRIGAN Plant Pat. 2,504
AZALEA PLANT
Filed Dec. 26, 1963
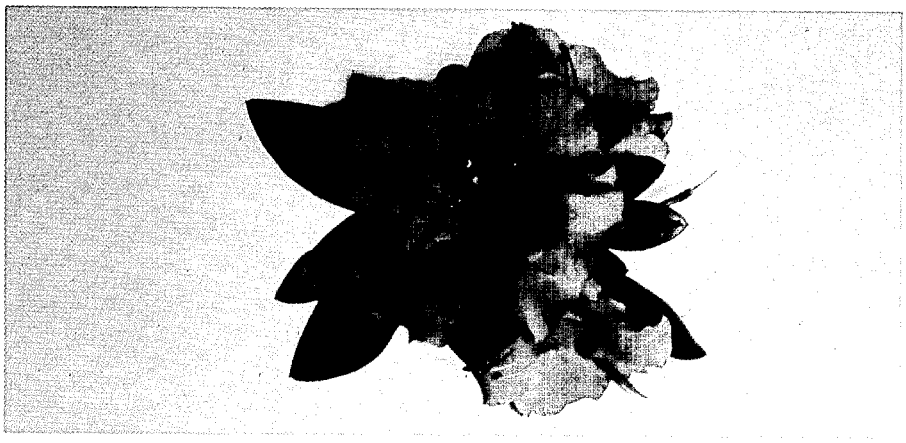
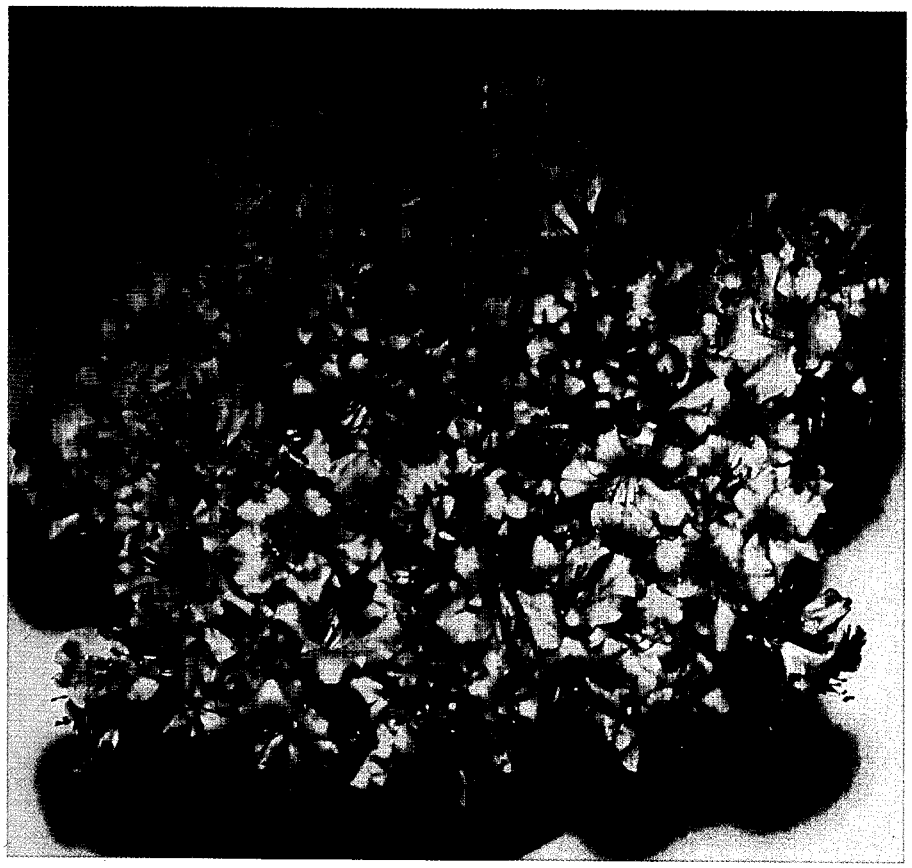

United States Patent Office

Plant Pat. 2,504
Patented May 4, 1965

2,504
AZALEA PLANT

Howard Kerrigan, 3003 Totterdell St., Oakland, Calif.

Filed Dec. 26, 1963, Ser. No. 333,778
1 Claim. (Cl. Plt.—57)

This disclosure concerns a new and distinct variety of azalea plant of the florists' forcing type possessing a combination of desirable characteristics ordinarily shared by the Belgian Indica azaleas, the Kurume azaleas and the Sanders hybrids but not heretofore found in combination in the same plant. This variety was developed by me at Oakland, California, in 1948 as a consequence of breeding efforts begun in 1943.

The main objective of this breeding program was the production of a new variety of florists' forcing azalea which combined the desirable features of the Belgian Indica azaleas, the Kurume azaleas and the Sanders hybrids in such a way as to yield a hose-in-hose flowered azalea of deep unfading red color, possessing extra-ordinary substance, with the profuse blooming habit of the Kurume type, the large flower of the Belgian Indica type and a significantly greater vigor and rate of growth than is available in the trade. In addition a heavily branched plant, that would be naturally compact but a plant bearing foliage of large size and rich color was sought.

These objectives were achieved in this variety which is a hand pollinated seedling of the variety known in the trade as Vuylsteke (Mme. Charles Vuylsteke, not patented), the seed parent and the variety Lentengroot (not patented), the pollen parent.

My new variety does not closely resemble either parent and the particular combination of characters present in the variety are essentially new in florists' azaleas. While the general flower form is similar to the pollen parent the size of the flower of my variety is much greater, of the order of 50–60%. My variety is profusely self branching and of rapid growth. The foliage is much larger than either parent. The intensity and durability of the color and its resistance to fading as it ages, makes it exceptionally suited for forcing. The flower substance is approximately twice that of Lentengroot and is so heavy as to feel almost leathery to the touch. The unusually large hose-in-hose flower with its perfect complement of stamens, its intensity and clarity of color and its exceptional bud set make my new variety particularly effective as a florist plant.

All of the characteristics of my new variety have proven consistent and stable through a continuous sequence of asexual generations begun in 1952 at Oakland, California. Propagation of this clon has been by soft wood cuttings.

The following are detailed horticultural and botanical descriptions of my new azalea plant. The color designations are those employed in the Horticultural Colour Chart issued by Wilson Colour Ltd. in collaboration with the Royal Horticultural Society.

*Horticultural description*

Robust upright small shrub to 30 inches tall and 20 inches across. Heavily branched, the stems heavy and stout about twice the diameter of the average Belgian Indica. Stems lightly covered with nearly black hairs. Color of the stems straw when young, shiny tan streaked green when mature. Internodes of strong growth quite long, shoots of well grown plants somewhat coarse unless properly pruned.

The foliage is very large, up to three inches long and an inch wide. The color of the leaves is light Ivy Green (HCC 0001060/5) above and Spinach Green (HCC 0960/5) below. The leaves are petiolate lightly pubescent below. The hairs are chestnut colored and flat, large, slender and stand out against the ground color of the leaf.

The inflorescence bears 3–4 flowers, all of which open at approximately the same time.

The flower buds are Cardinal Red (HCC 822/1), 1 5/16 inches long at opening. The flower type is single, hose-in-hose (terminology of Lee, F. P. et al. 1952. The Azalea Handbook of the American Horticultural Society.)

The calyx is imperfectly corolliform five lobed with the lobes deeply indented. The mature calyx is about half the size of the corrolla and is moderately to heavily pubescent on the outside.

The corolla is Blood Red (HCC 820/3) and extraordinarily deeply saturated with pigment. The lower half of the upper three corolla lobes are marked deep Chrysanthemum Crimson (HCC 824/1) as is the upper portion of the throat. The corolla is 2¾ inches across and 1½ inches deep. The tube is relatively long (¾ inch) and flaring but not nearly as flaring as a typical Belgian Indica. The corolla lobes are large, 1 inch long by 1¼ inches wide somewhat wavy. The reverse of the corolla is satiny, smooth while the inside is dull. The substance of the corolla is approximately twice that of the ordinary florists' azalea, waxy and extremely durable.

The stamens are eight in number 1½ inches long. The filaments are Blood Red. The anthers are brown.

The pistil is 1½ inches long. The stigma is large, 3/32 inch across, multiple lobed and faces outward rather than upward. The style is Blood Red stout barely curved, sometimes almost straight, gradually flaring towards its base with the lower portion bearing glandular hairs. The ovary is red, moderately pubescent.

*Botanical description*

Small upright semi-evergreen shrub to 30 inches. Profusely branched. The stems stout with relatively long internodes, straw colored when young, tan with greenish striations when old. Mature epidermis sub-nited. The young stems densely pubescent. The strigae are nearly black with sub-hyaline margins, entire, long lanceolate.

The foliage is large, 2¾ in. long by 1 5/16 inch wide on strong shoots. The petioles are ⅝ inch long sub-stipulate, lightly pubescent. The lamina is dark green above, lighter below. The upper surface is glaucous. The leaf shape is oblongate-oblanceolate. The margin is entire, ciliate with the apex conspicuously bluntly mucronate. The pubescence of the leaf is chestnut colored and conspicuous against the ground color of the leaf.

The inflorescence bears three to four flowers all reaching anthesis at approximately the same time.

The pedicel is short, 5/16 inch long stout, reddish proximally, becoming lt. green distally, pubescent. The calyx is subcorolliform, imperfect, basically five lobed but with each lobe deeply dissected into four or five secondary lobes, 1⅛ inches deep by about as wide, moderately to heavily pubescent on the reverse, glabrous within with some crimson markings dorsally.

The corolla is Blood Red, moderately flared, 2¾ inches across and 1½ inches deep; five lobed, the lobes are proportionately large, 1 inch long by 1¼ inches wide, auriculate, the margins moderately undulate, the tube is long, ¾ inch moderately flaring, marked crimson dorsally within. The deep crimson marking extends distally to the bases of the three dorsal lobes. The tissue of the corolla is heavy, thick, and leathery in texture. The reverse of the corolla is satiny while the obverse is glaucous.

The stamens are eight, 1½ inches long, Blood Red.

The anthers are brown, small, about 3/64 inch long. The pistil is 1½ inches long. The style is Blood Red, fasciated, straight or essentially so, at most only barely curved, glandular hispid proximally. The stigma is dark crimson, large, patent, with many small lobes. The ovary is red, moderately to densely setose.

Having disclosed my invention in the above descriptions and in the accompanying drawings which are as accurately representative of the natural colors as available methods will permit and which substantially illustrate the distinctive characteristics of my new variety to the extent that they may be disclosed by this means what I claim is new and patentable is:

A new and distinct variety of florists' forcing azalea which combines in a unique fashion many desirable characteristics of the Belgian Indica azaleas, the Kurume azaleas and the so-called Sanders hybrids, particularly the combination of a large hose-in-hose flower of intense Blood Red coloration possessing much greater substance and color stability than any other azalea of its color and type, borne in great profusion on a large, heavily branched, vigorous plant, which is easy to propagate and grow and which is covered with an abundance of very large dark green leaves.

No references cited.

ABRAHAM G. STONE, *Primary Examiner.*